United States Patent
Adams et al.

(10) Patent No.: US 9,974,900 B2
(45) Date of Patent: May 22, 2018

(54) DOSE REQUEST SYSTEMS AND METHODS

(71) Applicant: Smiths Medical ASD, Inc., Plymouth, MN (US)

(72) Inventors: Grant Adams, Plymouth, MN (US); Larry Zalesky, Plymouth, MN (US)

(73) Assignee: Smiths Medical ASD, Inc., Plymouth, MN (US)

( * ) Notice: Subject to any disclaimer, the term of this patent is extended or adjusted under 35 U.S.C. 154(b) by 0 days. days.

(21) Appl. No.: 15/327,859

(22) PCT Filed: Jul. 15, 2015

(86) PCT No.: PCT/US2015/040527
§ 371 (c)(1),
(2) Date: Jan. 20, 2017

(87) PCT Pub. No.: WO2016/014311
PCT Pub. Date: Jan. 28, 2016

(65) Prior Publication Data
US 2017/0197025 A1    Jul. 13, 2017

Related U.S. Application Data (60) Provisional application No. 62/026,855, filed on Jul. 21, 2014.

(51) Int. Cl.
*A61M 5/14* (2006.01)
*A61M 5/142* (2006.01)
(Continued)

(52) U.S. Cl.
CPC ......... *A61M 5/142* (2013.01); *G06F 19/3468* (2013.01); *A61M 2005/1405* (2013.01);
(Continued)

(58) Field of Classification Search
CPC ...... A61J 7/0038; A61J 7/0053; A61J 7/0076; A61M 5/142; A61M 5/1723;
(Continued)

(56) References Cited

U.S. PATENT DOCUMENTS 5,445,621 A    8/1995    Poli et al.
5,735,263 A    4/1998    Rubsamen et al.
(Continued)

FOREIGN PATENT DOCUMENTS

WO    WO 2013/158712 A1    10/2013

OTHER PUBLICATIONS

International Search Report for corresponding International Application No. PCT/US2015/040527 dated Oct. 26, 2015; 5 pages.
(Continued)

*Primary Examiner* — Ali Neyzari
(74) *Attorney, Agent, or Firm* — Patterson Thuente Pedersen, P.A.

(57) ABSTRACT

A dose request device for a medicament delivery device can include a housing, a dose request button, a short-range non-contact identifier, a communication interface configured to communicate with the medicament delivery device, and a controller. The short-range non-contact identifier can be configured to be capable of reading an identification code from a tag when the tag is disposed within a first range and not to be able to read the identification code from the tag when the tag is disposed beyond a second range. The controller can be configured and programmed to determine whether the identification code read by the short-range non-contact identifier matches any authorized identification code of a set of one or more authorized identification codes, and if so, and if the dose request button is pressed, the
(Continued)

controller can then communicate a dose request to the medicament delivery device via the communication interface.

21 Claims, 4 Drawing Sheets

(51) Int. Cl.
  *G06F 19/00* (2018.01)
  *H04W 4/00* (2018.01)
(52) U.S. Cl.
  CPC .............. *A61M 2205/3569* (2013.01); *A61M 2205/3584* (2013.01); *A61M 2205/50* (2013.01); *A61M 2205/502* (2013.01); *A61M 2205/52* (2013.01); *A61M 2205/6009* (2013.01); *A61M 2205/6054* (2013.01); *A61M 2205/8206* (2013.01); *A61M 2209/01* (2013.01); *H04W 4/008* (2013.01)
(58) Field of Classification Search
  CPC .. A61M 2005/1405; A61M 2205/3569; A61M 2205/3584; A61M 2209/01; A61M 15/008; A61M 2205/50; A61M 2205/6054; A61M 2205/6009; A61M 2205/52; A61M 2205/502; A61M 2205/8206; G06F 19/3468; G07F 17/0092
  USPC ............................................. 340/5.62; 604/59
  See application file for complete search history.

(56) References Cited

U.S. PATENT DOCUMENTS

| | | | |
|---|---|---|---|
| 5,971,594 A | 10/1999 | Sahai et al. | |
| 6,263,259 B1 | 7/2001 | Bartur | |
| 7,668,731 B2 | 2/2010 | Martucci et al. | |
| 7,766,863 B2 | 8/2010 | Gillespie, Jr. et al. | |
| 7,806,852 B1 | 10/2010 | Jurson | |
| 7,896,192 B2 | 3/2011 | Conley et al. | |
| 8,219,413 B2 | 7/2012 | Martinez et al. | |
| 8,357,114 B2 * | 1/2013 | Poutiatine | A61J 7/0038 604/59 |
| 8,512,314 B1 | 8/2013 | Candiotti | |
| 8,551,038 B2 | 10/2013 | Tsoukalis | |
| 8,574,189 B2 | 11/2013 | Poutiatine et al. | |
| 8,630,722 B2 | 1/2014 | Condurso et al. | |
| 8,655,676 B2 | 2/2014 | Wehba et al. | |
| 8,905,964 B2 * | 12/2014 | Poutiatine | A61J 7/0038 604/59 |
| 9,066,847 B2 * | 6/2015 | Poutiatine | A61J 7/0023 |
| 9,504,629 B2 | 11/2016 | Blomquist et al. | |
| 9,629,955 B2 | 4/2017 | Bresina et al. | |
| 2002/0038392 A1 | 3/2002 | De La Huerga | |
| 2005/0177096 A1 | 8/2005 | Bollish et al. | |
| 2007/0186923 A1 | 8/2007 | Poutiatine et al. | |
| 2007/0299687 A1 | 12/2007 | Palmer et al. | |
| 2008/0203107 A1 | 8/2008 | Conley et al. | |
| 2009/0014458 A1 | 1/2009 | Heffron | |
| 2009/0209938 A1 | 8/2009 | Aalto-Setälä | |
| 2010/0174229 A1 | 7/2010 | Hsu et al. | |
| 2013/0088328 A1 | 4/2013 | DiMartino et al. | |
| 2014/0194817 A1 | 7/2014 | Lee et al. | |

OTHER PUBLICATIONS

Written Opinion of the International Searching Authority for corresponding International Application No. PCT/US2015/040527 dated Oct. 26, 2015; 7 pages.
Search Report dated Mar. 15, 2018 for EP Application No. 15824119.0, 8 pages.

* cited by examiner

DOSE REQUEST SYSTEMS AND METHODS

CROSS REFERENCE TO RELATED APPLICATIONS

The present application is a National Phase entry of PCT Application No. PCT/US2015/040527, filed on 15 Jul. 2015, which claims priority to U.S. Provisional Patent Application No. 62/026,855, filed on 21 Jul. 2014, which are hereby fully incorporated herein by reference.

TECHNICAL FIELD

This disclosure relates to medicament delivery, and more particularly, to systems and methods for requesting doses of a medicament.

BACKGROUND

A variety of medical devices for medicament delivery are known. Such devices may be categorized according to how administration of a medicament is controlled: self-administered by the patient, by machine control programmed by a care provider, or by some combination—for example, administered by machine upon demand by a patient, in some cases subject to limits established by a care provider. Such administration by patient demand may be provided by so-called patient-controlled analgesia, or "PCA," systems. In the context of this disclosure, PCA may also refer to patient-controlled administration of non-analgesic medication delivery.

PCA infusion pumps have demonstrated their usefulness over a number of years. PCA pumps are typically designed to permit a patient to safely self-medicate with pain medications. Under the care of a healthcare practitioner, a patient using a PCA pump may receive a dose of medication by activating a control on or connected to the pump such as a push-button dose request switch. Such activation on demand by the patient may start a pumping mechanism in the PCA pump that delivers, for example, a measured dose of a fluidic drug (e.g., a liquid narcotic medication) to the patient via an intravenous or other fluid line within an allowable time interval. If a PCA command is activated during a time interval in which an allowable dose has already been administered, the delivery of a subsequent dose may be "locked out" until an appropriate time interval has passed, thereby safely preventing the patient from taking more than a maximum allowable dose of medication during a time interval. PCA pumps may provide other safety features to patients individually or in various combinations, such as, for example, enforcing maximum numbers of self-administered doses over programmable time periods and enforcing maximum amounts of medicaments delivered over programmable time periods. PCA pumps may also provide other functions, such as recording and reporting the volume of the medicament delivered over selected time intervals.

Recently, additional modes of patient-controlled medication delivery have been proposed or made available. For example, WO 2013/158712, "Medication Dispensers," describes a medication dispenser configured for dispensing substantially solid medication in response to activation of a medication dose request device. Solid medication PCA dispensers may share some characteristics with PCA infusion pumps, but may also present new challenges for medication management.

In view of the increasing prevalence of patient controlled analgesia, as well as the increasing diversity of on-demand medication dispensing or delivery systems, there is a need to improve PCA systems to result in appropriate delivery of medications to patients.

SUMMARY

This disclosure relates to medicament delivery, and more particularly, to systems and methods for requesting doses of medicaments.

In an illustrative but non-limiting example, the disclosure provides a dose request device for a medicament delivery device that can include a housing, a dose request button associated with the housing, a short-range non-contact identifier associated with the housing, a communication interface configured to communicate with the medicament delivery device, and a controller operatively coupled to the dose request button, the short-range non-contact identifier, and the communication interface. The short-range non-contact identifier can be configured to be capable of reading an identification code from a tag when the tag is disposed within a first range and not to be able to read the identification code from the tag when the tag is disposed beyond a second range. In some cases, the second range can be about 15 cm. The controller can be configured and programmed to determine whether the identification code read by the short-range non-contact identifier matches any authorized identification code of a set of one or more authorized identification codes, and if the identification code read by the short-range non-contact identifier matches any authorized identification code of the set of one or more authorized identification codes, and if the dose request button is pressed, communicate a dose request to the medicament delivery device via the communication interface.

In some cases, when the controller communicates the dose request to the medicament delivery device, the controller also communicates that the dose request is an authorized dose request. In some cases, when the controller communicates the dose request to the medicament delivery device, the controller also communicates the identification code read by the short-range non-contact identifier to the medicament delivery device.

In some examples, the controller can be configured and programmed to, if the identification code read by the short-range non-contact identifier does not match any authorized identification code of the set of authorized identification codes, and if the dose request button is pressed, not communicate the dose request to the medicament delivery device via the communication interface. In some other examples, under such conditions, the controller can be configured and programmed to communicate a non-authorized dose request to the medicament delivery device via the communication interface. Additionally, the controller can be configured and programmed to communicate a non-authorized dose request to the medicament delivery device along with the identification code read by the short-range non-contact identifier.

In some examples, the controller can be configured and programmed to, if the short-range non-contact identifier fails to read an identification code, and if the dose request button is pressed, not communicate the dose request to the medicament delivery device via the communication interface. In some other examples, under such conditions, the controller can be configured and programmed to communicate a non-authorized dose request to the medicament delivery device via the communication interface. In some other examples, under such conditions, the controller can be configured and programmed to communicate a non-identified dose request to the medicament delivery device via the communication interface.

In some examples, the communication interface can be configured to communicate with the medicament delivery device via a wired connection. In some examples, the communication interface can be configured to communicate with the medicament delivery device via a wireless connection.

In some cases, the short-range non-contact identifier is an RFID device, and the tag is an RFID tag.

In some examples, the controller can be configured and programmed to command the short-range non-contact identifier to attempt to read the identification code from the tag when the dose request button is pressed. Optionally, the controller can be configured and programmed to command the short-range non-contact identifier to attempt to read the identification code from the tag when the dose request button is pressed only if a time interval since a most recent preceding match of an authorized identification code exceeds a predetermined time interval. In some examples, the short-range non-contact identifier can be configured to periodically attempt to read the identification code from the tag, either under command from the controller, or independently of the controller.

The dose request device can include a memory operatively coupled to the controller. In some cases, the controller can be configured and programmed to store in the memory a log of presses of the dose request button along with, for each of the presses, a corresponding identification code or a lack of identification code.

The dose request device can include an indicator disposed with the housing that communicates an identification and/or dose request status.

In some examples, the dose request does not identify a type of medicament requested.

In another illustrative but non-limiting example, the disclosure provides a medicament delivery system that includes a medicament delivery device and a dose request device. The medicament delivery device can include a container configured to house a plurality of doses of a medicament, a controller configured to command release of a dose of the medicament upon receipt of a dose request if dose release criteria are satisfied, and a communication interface operatively coupled to the controller. The communication interface can be configured to receive a dose request from external the medicament delivery device and relate the dose request to the controller. The dose request device can include a housing, a dose request button disposed with the housing, a short-range non-contact identifier associated with the housing, a communication interface configured to communicate with the medicament delivery device, and a controller operatively coupled to the dose request button and the short-range non-contact identifier. The short-range non-contact identifier can be configured to be capable of reading an identification code from a tag when the tag is disposed within a first range and not being able to read the identification code from the tag when the tag is disposed beyond a second range. The controller can be configured and programmed to determine whether the identification code read by the short-range non-contact identifier matches any authorized identification code of a set of one or more authorized identification codes, if the identification code read by the short-range non-contact identifier matches any authorized identification code of the set of one or more authorized identification codes, and if the dose request button is pressed, communicate a dose request to the medicament delivery device via the communication interface.

In some examples, the medicament delivery device of the medicament delivery system can be configured to house and release only a single variety of medicament. In some examples, the medicament delivery device includes an infusion pump. In some examples of the medicament delivery system, the dose of the medicament is provided in an orally-ingestible solid.

In yet another illustrative but non-limiting example, the disclosure provides a method of providing a substance from a medicament delivery device. The medicament delivery device can be communicatively coupled to a dose request device. The dose request device can include a housing, a dose request button disposed with the housing, a short-range non-contact identifier associated with the housing, a communication interface configured to communicate with the medicament delivery device, and a controller. The method can include (without a particular temporal sequence necessarily being implied by the following order of description): the short-range non-contact identifier attempting to read an identification code from a tag, where the short-range non-contact identifier can be configured to be capable of reading identification codes from tags disposed within a first range and not being able to read identification codes from tags disposed beyond a second range; the controller determining whether the identification code read by the short-range non-contact identifier matches any authorized identification code of a set of one or more authorized identification codes; the controller, if the dose request button is pressed and if the identification code read by the short-range non-contact identifier matches any authorized identification code of the set of one or more authorized identification codes, communicating a dose request to the medicament delivery device via the communication interface; and the medicament delivery device delivering a dose of the substance after receiving the dose request from the communication interface of the remote dose apparatus. The method can further include the medicament delivery device subsequently delivering another dose of the substance after receiving another dose request from the communication interface of the dose request device.

The above summary is not intended to describe each and every example or every implementation of the disclosure. The Description that follows more particularly exemplifies various illustrative embodiments.

BRIEF DESCRIPTION OF THE FIGURES

The following description should be read with reference to the drawings. The drawings, which are not necessarily to scale, depict several examples and are not intended to limit the scope of the disclosure. The disclosure may be more completely understood in consideration of the following description with respect to various examples in connection with the accompanying drawings, in which.

DESCRIPTION

The following description should be read with reference to the drawings, in which like elements in different drawings may be numbered in like fashion. The drawings, which are not necessarily to scale, depict selected examples and are not intended to limit the scope of the disclosure. Although examples of construction, dimensions, and materials may be illustrated for the various elements, those skilled in the art will recognize that many of the examples provided have suitable alternatives that may be utilized.

With the use of PCA come attendant risks of misuse, mal-use, abuse, and drug theft. In many or most implementations of PCA, drug delivery may take place without the presence and/or direct observation of a responsible medical professional. A patient may be provided with a PCA medicament delivery device in a relatively uncontrolled area of a hospital or other healthcare site where they may be visited by friends, relatives, and others. In some cases, patients may use PCA devices at home or other settings, such as a hospice facility. Inappropriate use of a PCA medicament delivery device may occur in a number of ways. In some cases, a well-intentioned but perhaps uninformed relative or friend may attempt to utilize a PCA request device on behalf of or as a proxy for the patient, such as for example when the patient is sleeping or unconscious. Such "PCA by proxy" actions can lead to significant injury to the patient, or even death. In other cases, unauthorized actuation of PCA mechanisms may be used to steal or otherwise misappropriate drugs such as narcotics. While a PCA infusion pump generally entails a physical connection between the patient and the pump via an medication delivery tubing set, other PCA delivery modes such as solid medication delivery devices may operate outside this physical connection and association that nominally would have existed between patient and PCA device, creating new avenues for misdirection of drugs to other than the medically-intended recipient. Other scenarios are also contemplated in which an unauthorized individual attempts to actuate a PCA dosing mechanism, consciously or not, and with or without malicious intent.

The present disclosure provides dose request devices, systems, mechanisms, and methods that identify (or attempt to identify) a user who requests a dose. With correlated identification and dose request information, a medicament delivery device can be controlled such that a dose may be provided only when an authorized/authenticated user is identified as having made the request, reducing the possibility of delivering drugs inappropriately.

Within the scope of this disclosure, "medicament delivery device" may refer to an apparatus configured to deliver to an individual a medicament, which can be any fluid, solid, or other substance prescribed: to cure or treat symptoms of an illness or medical condition; as a preventative measure; or to otherwise enhance physical or mental well-being.

Figure 1:
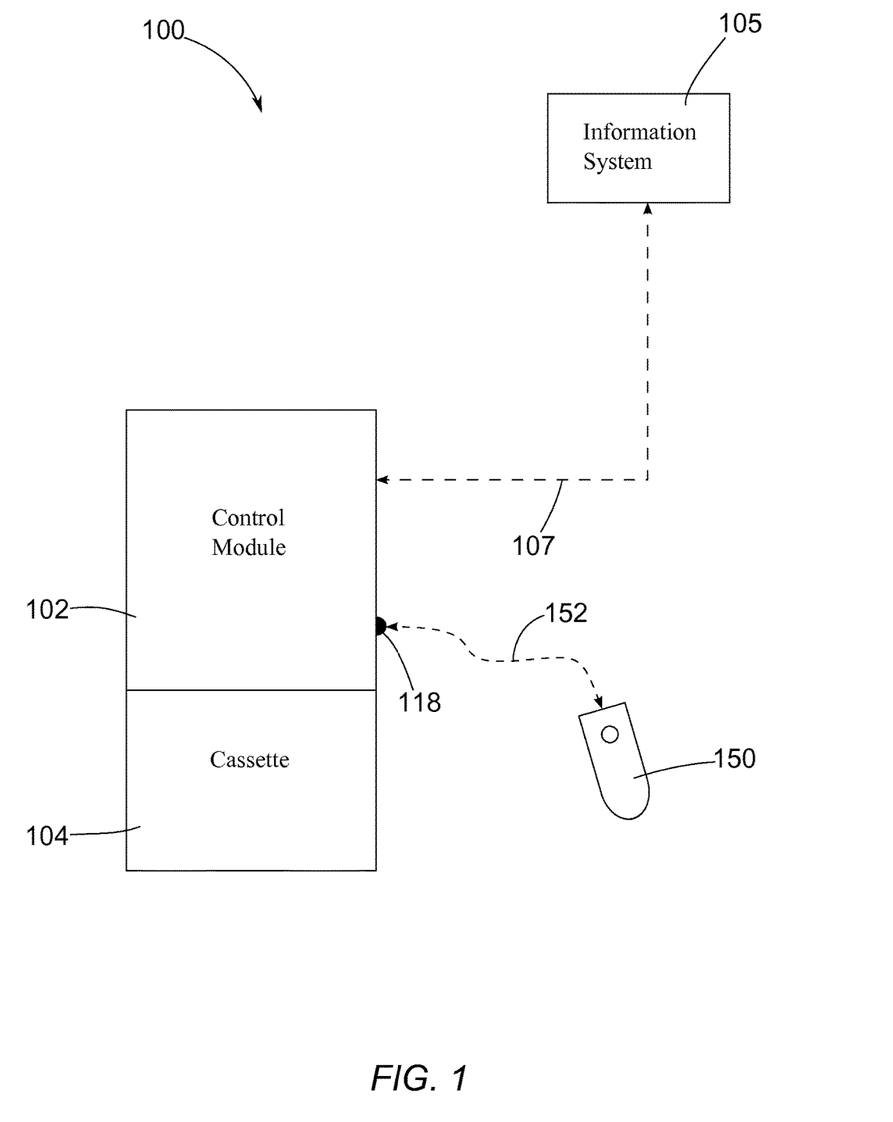
FIG. 1 is a schematic block diagram of an example of a medicament delivery system.

FIG. 1 is a schematic block diagram of an example of a medicament delivery system 100 that includes a medicament delivery device having a control module 102 and an optional cassette 104. Cassette 104 can be a replaceable container configured to house and deliver a plurality of doses of a medicament under the control of control module 102. Various implementations of cassette 104 can store and deliver medicaments in any suitable form. For example, some examples of cassette 104 can include a reservoir configured to store a liquid infusate that can be delivered to a patient through an infusion set or catheter (not shown). In other examples, a cassette 104 can include a dispensing device configured to dispense substantially solid medication (for example, orally-ingestible solids), as described, for example, in PCT Publication WO 2013/158712, "Medication Dispensers." In another example, replaceable cassette 104 can include a dispensing device configured to dispense medication in an inhalable form under the control of control module 102. In some examples, cassette 104 can be configured to deliver multiple separate doses of substantially the same medicament with each dose. In some examples, cassette 104 can be configured to house and dispense only a single type of medicament.

Some examples of individual cassettes can enclose a supply, reservoir, magazine, or other storage space that can hold an entirety of the quantity of medication or substance that the individual cassette may be configured to dispense. Some examples of other cassettes can be configured to dispense medication or substances drawn from a non-enclosed supply or reservoir such as an external conventional IV (intra-venous) bag. It may be appreciated that aspects of the present disclosure may be practiced with a medicament delivery device that includes a control module 102 and any suitable cassette 104, where the cassette can be configured to dispense any suitable medication under the control of the control module. In some examples, a syringe infusion pump may be considered to be a control module and a syringe operable with the syringe infusion pump may be considered to be a cassette or replaceable container.

In some examples, aspects of the present disclosure may be practiced with a medicament delivery device that includes a control module, but without a replaceable or detachable cassette. For example, a medicament delivery device control module could deliver a substance from a non-removable/replaceable enclosed storage volume, or could deliver a substance drawn from a non-enclosed supply or reservoir such as an IV bag, without the need of a removable/replaceable cassette or cassette-like component. In some examples, the medicament delivery device can be configured to house and release only a single variety of medicament.

Medicament delivery system 100 can be communicatively coupled to an information system 105, which can be an electronic medical record ("EMR") system, an electronic Hospital Information System ("HIS"), or another appropriate computing system, via any appropriate communication link 107, which can be wired or wireless. Any appropriate information can be transferred between control module 102 and the information system 105 via the communication link 107.

The control module 102 can include a controller (not shown) configured to command release of a dose of medicament (from cassette 104 or via other mechanism) upon receipt of a dose request, as further described elsewhere herein, if dose release criteria are satisfied. Control module 102 also can include a communication interface (not shown) operatively coupled to the controller. The communication interface of control module 102 can be configured to receive a dose request externally from the medicament delivery device and relate the dose request to the controller.

Medicament delivery system 100 can include a dose request device 150, which can be a novel dose request device of the present disclosure described in further detail herein. Dose request device 150 can be communicatively coupled to control module 102 (via, for example, the communication interface of the control module) via any appropriate communication link 152, which can be wired or wireless. Dose request device 150 can be configured to accept input from a patient in PCA fashion or other authorized individual and relay a request for a dose of medication to control module 102. In some examples, a request for a dose of medication can be communicated to a control module 102 from a dose request device 150 by way of a dose request device jack 118 of the control module. Some known dose request devices may be referred-to as remote dose cords ("RDC"s), with a corresponding dose request device jack being referred-to as a remote dose cord jack. It is to be understood that a remote dose "cord" may refer to a remote dose request device that includes both a cable and an attached handheld unit such as device 150.

Figure 2:
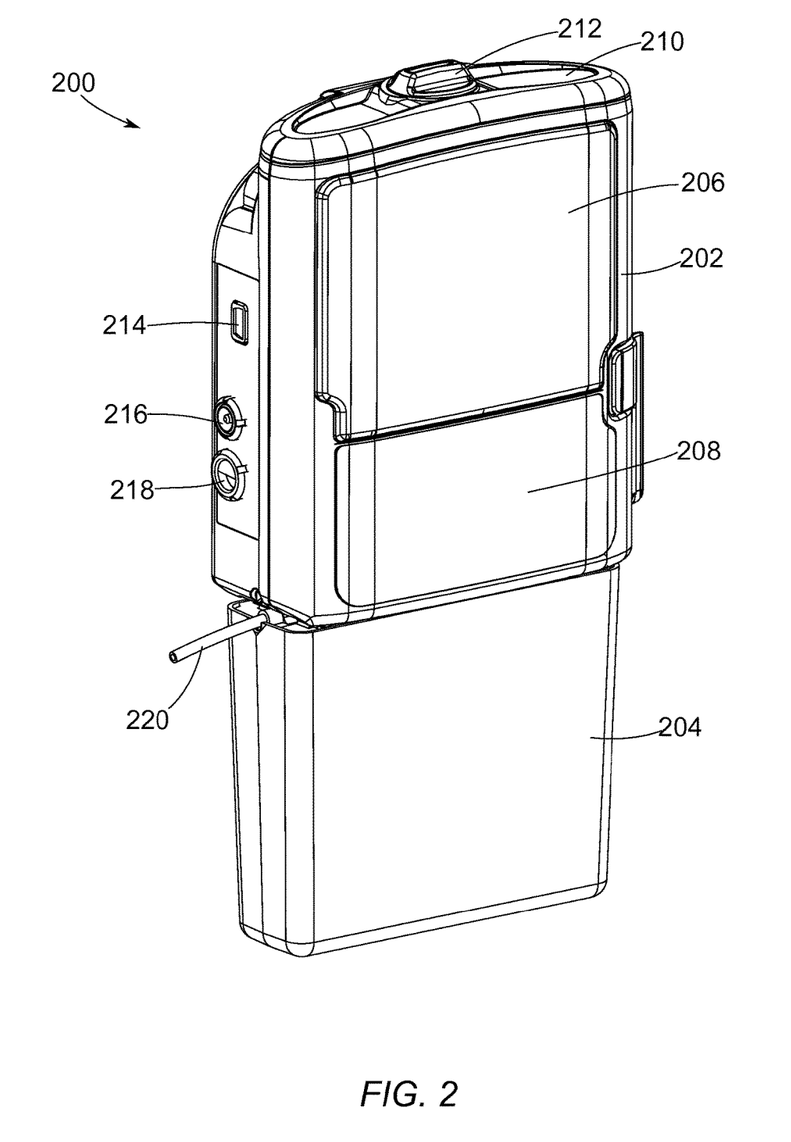
FIG. 2 is a schematic perspective view of an example medicament delivery device that illustrates some of the features of the system of FIG. 1.

FIG. 2 is a schematic perspective view of an example medicament delivery device 200 that exhibits at least some of the features of the medicament delivery device of system 100 of FIG. 1. Medicament delivery device 200 includes a control module 202 and an optional cassette 204. Medicament delivery device 200 may be a CADD® (Computerized Ambulatory Drug Delivery) device from Smiths Medical ASD, Inc., although the teachings of the present disclosure are not limited to CADD® devices and may be practiced with any suitable medicament delivery device.

Control module 202 of medicament delivery device 200 can include a user interface having a display screen 206 and a control pad 208 (buttons, etc., of the control pad are not illustrated). Control module 202 can also include a battery door 210, including a knob 212 for locking and unlocking the door 210, which can cover a battery compartment in which batteries for internally powering the medicament delivery device 200 can be housed. In some examples, a combination battery and wireless communication module can be present approximately where battery door 210 is illustrated. Control module 202 can also include any of the following components: a power switch (not visible); an input/output port 214 such as a USB port or other appropriate interface for connecting the control module to a computer having software designed to interface with the control module; a power jack 216 for connecting a power cord for externally powering device 200; and a remote dose cord jack 218, as aforementioned, for connecting a dose request device that provides a way to activate doses of patient-controlled analgesia/administration (PCA) from device 200.

Medicament delivery device 200 can include a replaceable cassette 204 that is a reservoir cassette housing a reservoir containing medication to be delivered to a patient. Tubing 220 can extend from the cassette 204 and communicate with an infusion set or catheter (not shown) to deliver the medication to the patient. The control module 202 can be used to control the flow of medication from the cassette. One example of such a cassette is the CADD® Medication Cassette Reservoir from Smiths Medical ASD, Inc., though other cassettes can be used in other examples. Control module 202 in conjunction with a replaceable cassette 204 that is a reservoir cassette can constitute major components of a medicament delivery system. Aspects of the present disclosure can be practiced with infusion pumps like or similar to the illustrated example of delivery device 200 of FIG. 2, and more generally with the example of delivery system 100 of FIG. 1.

The present disclosure describes dose request devices that can be configured to communicate with the delivery device of medicament delivery system 100 via dose request device jack 118 of control module 102, a more particular example of which is remote dose cord jack 218 of medicament delivery device 200. However, system 100 and device 200 are not limited to dose request devices that communicate via a jack such as jacks 118 and 218, nor are they limited to dose request devices configured for use with delivery devices such as the device of medicament delivery system 100 of FIG. 1 or medicament delivery device 200 of FIG. 2. Dose request devices incorporating aspects of the present disclosure can be used, for example, with infusion pumps or other medicament delivery devices that do not employ cassettes. Dose request devices having features of the present disclosure can be used with any suitable medicament delivery device.

Figure 3:
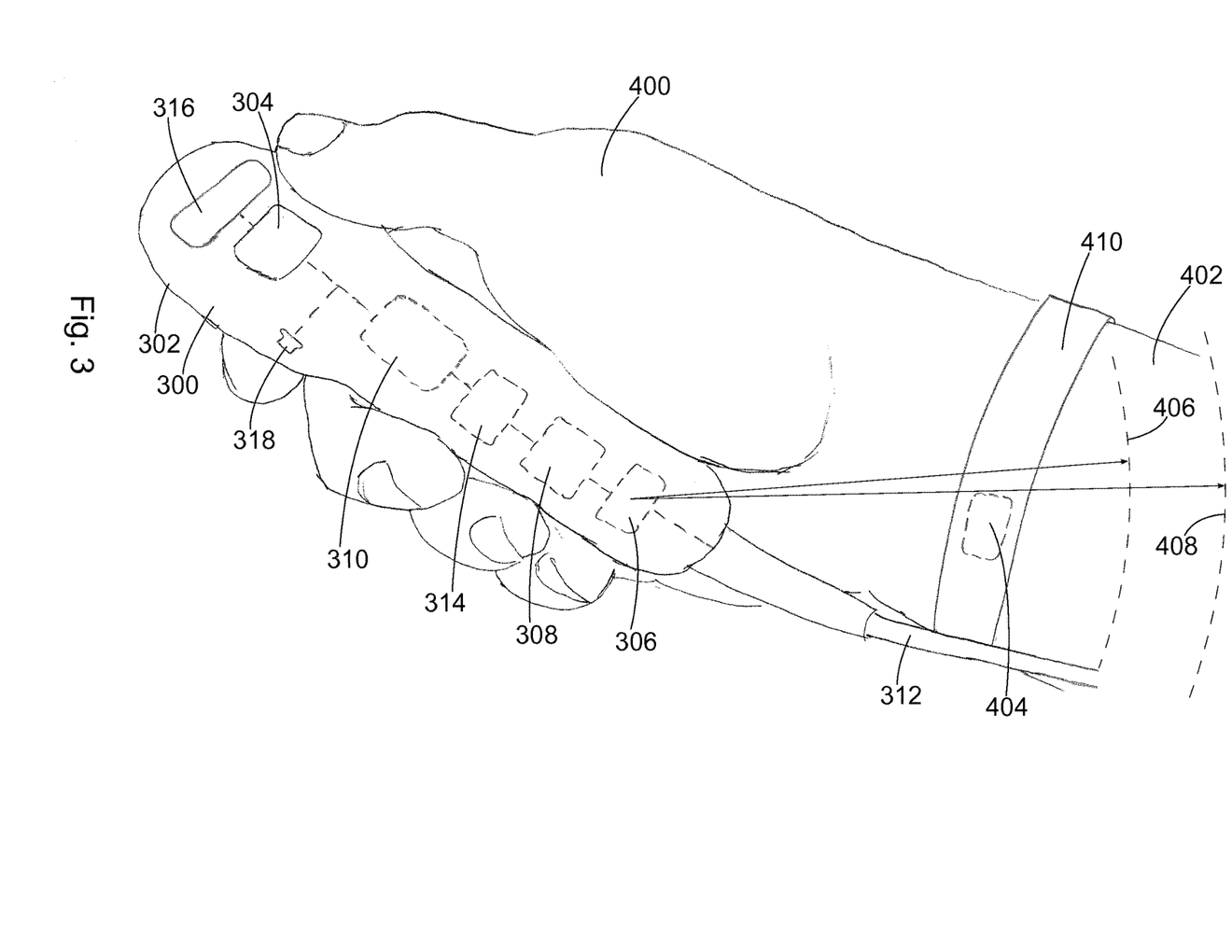
FIG. 3 is a schematic perspective view of an example of a dose request device configured to operate in conjunction with a medicament delivery device.

FIG. 3 is a schematic perspective view of an illustrative dose request device 300 configured to operate in conjunction with a medicament delivery device. Dose request device 300 can be used in any suitable medicament delivery system. For example, dose request device 300 can be used as dose request device 150 of delivery system 100 of FIG. 1, or can be coupled to delivery device 200 of FIG. 2, for example, via remote dose cord jack 218. In FIG. 3, dose request device 300 is illustrated in relation to a human hand 400 and arm 402. While FIG. 3 illustrates a particular physical form for a dose request device 300, this is merely by way of example, and dose request devices of the present disclosure can take any suitable physical form.

Dose request device 300 can include a housing 302 and a dose request button 304 disposed in or on the housing. Dose request device 300 can include a short-range non-contact identifier 306 associated with the housing. Dose request device 300 can also include a communication interface 308 configured to communicate with a medicament delivery device, such as by communicating to control module 102, and a controller 310 operatively coupled to the dose request button 304, the short-range non-contact identifier 306, and the communication interface 308. Various features of dose request device 300 are shown schematically in phantom lines, indicating that they may not be visible from outside of housing 302. Various features are illustrated as being linked by dotted lines, which schematically indicate operative couplings between said features. The operative couplings indicated by the dotted lines should not be considered limiting, and any appropriate operative couplings between features/components may exist. For example, while FIG. 3 may topologically appear to illustrate controller 310 as being operatively coupled to short-range non-contact identifier 306 through communication interface 308, this is merely for convenience of illustration, and controller 310 and identifier 306 can be coupled directly, or through a bus, etc., potentially bypassing interface 308.

Dose request device 300 can be a distinct device separate from a medicament delivery device with which it may be associated. Housing 302 of dose request device 300 can be distinct and separate from any housing of a medicament delivery device with which it may be associated. While dose request device 300 and a medicament delivery device can be physically connected by one or more cables, tethers, and the like, such connections may be selectively breakable. In some other instances, a dose request device or mechanism could be physically integrated with a medicament delivery device such that it cannot be readily separated from the medicament delivery device. Such an integrated dose request device/mechanism could otherwise be configured with the same features of any dose request device of the present disclosure.

Dose request button 304 can be any suitable button or device, sensor, or user input mechanism capable of detecting or sensing a press, touch, squeeze, or any other suitable activation motion or intentional manipulation, pressure, or indication. Any suitable technology can be employed for button 304. Button 304 can, for example, be a mechanical switch such as a domed membrane switch, or a touch sensor relying upon capacitance, resistance, or other physical principle. Dose request button 304 can have a fixed location relative to housing 302 of dose request device 300, but this is not limiting, and it can, for example, be a virtual button (such as on a touch-screen) with a changeable location. In some examples, dose request button 304 can be an unconventional button that may be "pressed" or otherwise actuated in any suitable manner. For example, the dose request button 304 could be implemented with a camera and suitable image processing, and "pressing" the button could be accomplished by a user executing a particular body motion, or by looking at a particular location in space or with a particular gaze pattern, or by any other suitable detectable intentional action of the user. In the present disclosure, a "press" of a dose request "button" may describe any intentional actuation of a dose request input mechanism by a user. In some examples, dose request button 304 can share hardware (such as, for example, a camera) with other components (such as, for example, short-range non-contact identifier 306) of dose request device 300.

Communication interface 308 can be structured and configured to communicate with a medicament delivery device in any suitable manner. Any suitable communication protocol can be used to communicate from dose request device 300 to a medicament delivery device. Wired and/or wireless connections can be employed by the communication interface 308. In some examples, communication interface 308 can include a cable 312 configured to mate with dose request device jack 118/218 of control module 102/202.

In some examples, a known dose request device jack presents a plurality of conductors to a known dose request device or known remote dose cord. A dose request button of such a known dose request device can include a single pole double throw (SPDT) switch having a common input line and first and second output signal lines. The SPDT switch can be configured as normally-closed for the first output signal line and normally-open for the second output signal line. Electrical power can be supplied from a control module to the known dose request device via the normally-closed first output signal line. In circumstances when the second output signal line is closed, power could be supplied via that route. Depression or actuation of the dose request button of the known dose request device can, in normal operation, reverse the states of the first and second output signal lines. This multiple output line arrangement can provide a measure of redundancy to prevent failure of a single output line from signaling an undesired dose request. Some examples of novel dose request devices of the present disclosure can be configured to interface with such a known dose request device jack that is configured to interface with known dose request devices. In such cases, the novel dose request devices of the present disclosure can substantially present to the known dose request device jack signals that emulate, from the perspective of the known dose request device jack, signals that would be presented by a known dose request device. Such backward-compatible novel dose request devices can thus advantageously provide new functionality to known medicament delivery devices without requiring modification of the known delivery devices.

Communication interface 308 can be configured to communicate with a medicament delivery device using a protocol that allows transmission of extended information beyond the simple button depressed/not depressed ("BD/ND") information of known dose request devices. Transmission of information, whether extended or simple, can involve one or more known standard technologies/architectures/protocols/etc., such as USB, TCP/IP, Ethernet, RS-232, WiFi, ZigBee, Bluetooth, NFC, IrDA, ANT, etc., and/or it can involve one or more novel and/or proprietary communication protocols. A communication port 318 can be operatively coupled to communication interface 308 of dose request device 300.

In some instances, it is contemplated that communication interfaces of backward-compatible novel dose request devices can be configured to transmit extended information via conductors that can interface to the conductors of a known dose request device jack. For example, extended information could be transmitted on an information signal overlaid upon the electrical power provided over a normally-closed first output signal line. In another example, information could be transmitted over the normally-open second output signal line. Such information transmission over the second output signal line could be performed when the second signal line is closed, as it nominally would be when indicating "button depressed" in the BD/ND protocol. Information could also be transmitted over the normally-open second output signal line when the second signal line is nominally open, by closing the second output line in a modulated manner that would not be interpreted by a known medicament delivery device as indicating "button depressed" in the BD/ND protocol (for example, while the normally-closed first signal line remains closed). Extended information in such cases can be receivable and usable by novel medicament delivery devices, whereas known delivery devices that are not configured to receive such information can simply function with the backward-compatible normally-closed/open switch logic also provided by the novel dose request device. In some other examples, a communication interface 308 of a novel dose request device can be configured to communicate via multiple communication channels. For example, a novel dose request device can include a communication interface 308 that provides simple BD/ND information via the protocol of a known dose request device jack, and extended information via any other suitable protocol/avenue. Any suitable communication interface and communication protocol(s)/technologies can be used in dose request devices of the present disclosure.

In some instances, a dose request device can include a device or dongle that attaches to a known dose request device jack, with the dongle providing at least part of a communication link with a remote portion of the dose request device. For example, a remote handheld portion of a dose request device can include at least a housing 302, dose request button 304, short-range non-contact identifier 306, and controller 310, and the communication interface 308 can include a wireless link between the remote handheld portion and the dongle, thereby providing a wireless dose request device capability to a known medicament delivery device having a wired known dose request device jack.

Communication interface 308 or another communication interface of dose request device 300 can be configured to provide communication between the dose request device 300 and other systems and/or devices other than medicament delivery devices. For example, communication interface 308 can provide communication (for example, via communication port 318, or via a wireless communication link) between the device and an EMR system and/or a computing device such as a personal computer, PDA, computing tablet, smartphone, or any other suitable device or information system. Dose request device can include a port or other interface (in addition to or as an alternative to port 318; not shown) to permit connection to or insertion of a memory device such as a USB drive, flash memory card such as any of the variants of SD (micro-, mini-, SDHC, SDXC, etc.), or any other suitable device. Any appropriate information may be transferred to or from the dose request device via these mechanisms, for example, as discussed elsewhere herein.

The short-range non-contact identifier 306 can be any suitable device employing any suitable technology. In some examples, the short-range non-contact identifier 306 employs radio-frequency identification (RFID) or near-field communication (NFC) technology. In other examples, the short-range non-contact identifier 306 can employ optics to read a barcode, QR code, or other optical code, and/or obtain an image for facial, iris, fingerprint, or other biometric recognition. The short-range non-contact identifier 306 can be capable of reading an identification code from a tag 404 when the tag is disposed within a first range 406 and not being able to read the identification code from the tag when the tag is disposed beyond a second range 408. When the short-range non-contact identifier 306 is an RFID device, the tag 404 can be an RFID tag. In FIG. 3, the tag 404 is illustrated as being integrated with a wristband 410, and is shown in phantom lines, suggesting that the tag may not be readily visible to an observer, though this is not required. A tag 404 that is not apparent to an observer may be advantageous, for example, in that both authorized and unauthorized users of the dose request device 300 might be kept unaware of the identification and authentication functionality of the dose request device, such that they may be less able to deliberately thwart it. An RFID tag can be disposed at or on an inner surface of a wristband, or entirely within inner and outer layers of a wristband, obscuring it from view. An optical code nominally can be visible, but could, by the nature of the coding, not be obvious as a code—hidden in plain sight, so to speak. Alternatively, an optical code could be written with "invisible" infra-red markings.

With the tag 404 disposed on the user's wrist, and the dose request device 300 held in the user's hand 400, the tag can be disposed within both the first and the second ranges of the short-range non-contact identifier 306. If the second range is sufficiently limited, the probability of the short-range non-contact identifier 306 reading an identification code from tag that is not in a wristband worn by a user handling the dose request device 300 can be decreased significantly. This may be desirable in the interest of verifying (or at least increasing the likelihood) that the person handling the dose request device 300 is an authorized user. As such, the second range can have a value of approximately 20 cm, 10 cm, 15 cm, 5 cm, or any other suitable value.

In some examples, reading sensitivity of the short-range non-contact identifier 306 can be anisotropic, being more sensitive in some spatial directions than others. Appropriate orientation of such a short-range non-contact identifier 306 can be used advantageously to reduce the likelihood that a tag not disposed on a user's wrist (or any other appropriate selected location) is read. An antenna of an RFID reader, for example, can be configured to be more sensitive in a given direction. A laser scanner, for example, can be very precisely controlled with regard to direction of operation. A camera generally can have a limited field-of-view, which may establish directional sensitivity, and can feature focus characteristics that can be exploited to control a range over which it can identify a target. In the context of the present disclosure, "range" may be understood to incorporate a directional aspect as well as a distance aspect, and descriptions such as "within a first range" may be further qualified by aspects such as "in a direction of interest"; "in a hemisphere oriented in a direction of interest", "in a pre-determined solid angle oriented in a direction of interest" where the solid angle has a value such as $2\pi$, $\pi$, $\pi/2$, or any other appropriate value. In some examples, the ranges of "within a first range" and "beyond a second range" may be described more precisely by the concepts of "within a first region" and "outside a second region," where the second region can enclose the first region.

The placement of the short-range non-contact identifier 306 relative to the housing 302 of dose request device 300 can be selected to result generally in its placement a position close to a user's wrist when the short-range non-contact identifier 306 is held by the user in a standard or usual orientation. The shape of the housing 302 and possibly other aspects of the short-range non-contact identifier 306 can be selected to encourage a user to hold it in a particular orientation (and discourage a user from holding it in a less desirable orientation), which may in turn result in an advantageous disposition of the short-range non-contact identifier 306 relative to the user's wrist. Those of skill in the art may readily contemplate such relatively ergonomic shapes and arrangements, for example, a pistol grip, a joystick, etc.

In some examples, a non-contact identifier 306 can operate in conjunction with another non-contact identifier or another identifier technology. For example, an RFID reader can read an RFID tag and a camera can capture one or more images used to read a barcode or perform facial and/or iris recognition. Correlated identification matches can be interpreted as increased likelihood that a correct identification of a user has been made. In another example, a camera can capture an image upon which image analysis is performed, for example, to establish that a wristband is disposed on an arm of a user pressing a dose request button of a dose request device. Such a scheme could substantially verify that a RFID identification code read in conjunction is that of an RFID tag disposed in the wristband on the user's wrist, which can also be interpreted as increased likelihood that a correct identification of a user has been made.

The controller 310 can be any suitable controller, microcontroller, microprocessor, or the like. Controller 310 can include or be operatively coupled to a memory 314 of the dose request device 300. Memory 314 can be any suitable memory of any suitable capacity, and can be a non-volatile memory such as flash, EEPROM, and so on. Memory 314 can store any suitable information, such as one or more authorized identification codes, activity logs, executable code, operational parameters, and so on. Controller 310 of dose request device 300 can be configured and programmed to execute, command, and/or perform any suitable actions, tasks, steps, and/or methods for controlling the dose request device. Other controllers or processors (not shown) can also be employed in dose request device 300 (for example, short-range non-contact identifier 306 and/or communication interface 308 can include one or more dedicated processors). Regardless, these other controllers or processors can be considered part of the controller or microprocessor component 310 of FIG. 3.

In an example operation, the short-range non-contact identifier 306 reads an identification code from a tag. The tag can be a tag 404 integrated with a wristband 410 on a user's wrist, but this is not necessary, and the tag may be provided separately from a wristband. Controller 310 can be configured and programmed to determine whether the identification code read by the short-range non-contact identifier matches an authorized identification code of a set of one or more authorized identification codes, which can be any authorized identification code of the set. If the identification code read by the short-range non-contact identifier 306 matches an authorized identification code, then if the dose request button 304 is pressed, the controller 310 can communicate a dose request to a corresponding medicament delivery device via the communication interface 308.

The communication of the dose request to the medicament delivery device can include different amounts of information in various examples. In some examples, dose request device 300 is connected to a known dose request device jack and can provide simple BD/ND information. From the perspective of the receiving medicament delivery device, the BD/ND information can be indistinguishable from that provided by a known remote dose cord that does not include any identification capability. In some other examples, extended information can be communicated. In some examples, when the controller 310 communicates the dose request to the medicament delivery device, it can communicate that the dose request is an authorized dose request, that is, a dose request associated with a determination that an identification code read by the short-range non-contact identifier 306 matches an authorized identification code. (As discussed elsewhere herein, in some cases non-authorized dose requests can be communicated when explicitly identified as non-authorized dose requests.) In some examples, when the controller 310 communicates the dose request to the medicament delivery device, it can also communicate to the delivery device the identification code that was read by the short-range non-contact identifier.

In some examples, it is contemplated that a dose request communicated by a dose request device 300 to a medicament delivery device does not identify a particular or specific drug, infusate, substance, or therapy that is being requested, but rather, simply communicates that a dose is requested. Such a dose request may be referred-to as a non-specific dose request or a binary dose request.

The controller 310 of dose request device 306 can be configured and programmed to respond to a variety of instances in which an identification code read by the short-range non-contact identifier 306 does not match any of a set of one or more authorized identification codes. In some such examples, when the dose request button 304 is pressed, the controller 310 does not communicate the dose request to the medicament delivery device via the communication interface 308. In cases in which a dose request device 300 is connected to a known dose request device jack, this means that BD/ND information in the form of "button not depressed" would be read at the known dose request device jack when dose request button 304 was pressed, but an identification code read by the short-range non-contact identifier 306 did not match an authorized identification code.

When extended information beyond BD/ND information can be communicated by the communication interface 308 of the dose request device 300, additional communication possibilities exist when an identification code read by the short-range non-contact identifier 306 does not match any of a set of one or more authorized identification codes and dose request button 304 is pressed. In some examples, when the dose request button 304 is pressed, the controller 310 can communicate a non-authorized dose request to the medicament delivery device via the communication interface. The delivery device can be configured and programmed to handle a non-authorized dose request in any suitable manner. It can, for example, maintain a log of non-authorized dose requests, and/or alert a caregiver to their occurrences. In some other examples, when the dose request button 304 is pressed, the controller 310 can communicate a non-authorized dose request to the medicament delivery device along with the identification code read by the short-range non-contact identifier. The delivery device can be configured and programmed to handle the non-authorized dose request along with any associated identification code provided therewith in any suitable manner.

In some cases, the dose request button 304 can be pressed, but the short-range non-contact identifier 306 may fail (or may have failed) to read any identification code at all. In some such instances, the controller 310 can be configured not to communicate the dose request to the medicament delivery device, or in other instances, it can communicate a non-authorized dose request to the delivery device. In yet other instances, it can communicate a non-identified dose request to the delivery device, with these possibilities communicated via the communication interface to the medicament delivery device and/or one or more systems such as an EMR or HIS system.

The short-range non-contact identifier 306 can read (or at least attempt to read) a tag at any appropriate time, under any appropriate circumstance. The controller 310 (which can be a central controller, or can be a de-centralized controller, such as a dedicated controller of the short-range non-contact identifier) can be configured and programmed to command the short-range non-contact identifier 306 to attempt to read the identification code from a tag when the dose request button 304 is pressed, meaning that the short-range non-contact identifier can be commanded to attempt to read an identification code from a tag as a consequence of the dose request button having been pressed, generally as soon as practicable after the button is pressed. In some examples, the controller 310 can be configured and programmed to command the short-range non-contact identifier 306 to attempt to read the identification code from a tag when the dose request button 304 is pressed only if a time interval since a most recent preceding match of an authorized identification code exceeds a predetermined time interval. In some examples, the short-range non-contact identifier is configured to periodically attempt to read the identification code from the tag, either under command from the controller, or independently of the controller. In some examples, a match of a code read by the short-range non-contact identifier 306 with an authorized identification code can be considered to be valid for a pre-determined time interval. In some such examples, if a match has been made and is still considered valid (i.e., the pre-determined time interval has not expired), then the controller 310 can be configured not to command the short-range non-contact identifier 306 to attempt to read an identification code regardless of other considerations such as button presses. In some examples, the controller 310 can be configured and programmed to command the short-range non-contact identifier 306 not to attempt to read the identification code from a tag when the dose request button is pressed excessively (for example, at a frequency substantially exceeding a frequency at which doses of a medicament might be delivered).

Dose request device 300 can include an indicator 316 disposed in or on housing 302 and operatively coupled to the controller 310. The indicator 316 can be a visual indicator, an audio indicator, a tactile indicator, or any other suitable indicator or combination of indicators. Indicator 316 can communicate any appropriate information, such as an identification status (e.g., an icon or a color could indicate when an authorized identification code has been read from a tag) and/or a dose request status (e.g., a beep could indicate that a dose request has been communicated, while a buzz could indicate that a button press did not result in a dose request communication). These are just some examples of ways in which an indicator could be incorporated with device 300.

Dose request device 300 with a short range non-contact identifier 306 can manage any related information in any suitable manner. As disclosed elsewhere herein, a dose request device 300 can communicate BD/ND information and/or extended information to a medicament delivery device that can include, without limitation, whether a dose request is authorized or not-authorized, and an identification code (authorized or not) associated with a dose request. In some examples, a dose request device 300 can communicate additional and/or other information to a medicament delivery device, such as identification codes read by the short-range non-contact identifier 306 (not all of which are associated necessarily with dose requests), time stamps for dose request button 304 presses and/or identification code readings, and any other relevant information. Any suitable combination(s) of information can be communicated. In some examples, controller 310 of dose request device 300 can be configured and programmed to store in memory 314 a log of any relevant information, such as a log of presses of the dose request button 304 along with, for each of the presses, a corresponding identification code or a lack of identification code, and/or any other relevant information. In various examples, appropriate information can be logged in memory 314 and/or communicated essentially in real-time as it is generated to a medicament delivery device and/or EMR or HIS system with which dose request device 300 is associated. In some examples, information can be communicated to a medicament delivery device and/or EMR system upon the occurrence of one or more types of events, such as button presses, attempts of the short range non-contact identifier to read a tag, and the like. In some examples, aggregated log information can be communicated to a medicament delivery device and/or EMR system upon demand or request, and/or according to a schedule.

Dose request device 300 can be configured to manage identification codes in any suitable manner. A list or set of authorized identification codes can be stored in and accessed from memory 314. In some examples, authorized identification codes can be stored in and accessed from an attached memory device such as a flash memory device. Authorized identification codes can be transferred to and/or from memory 314 from an operatively coupled memory device and/or via data connection to an external computing device or server such as an HIS or EMR system. In some examples, controller 310 can be configured and programmed to record or remove one or more authorized identification codes from memory 314 without attaching or otherwise connecting thereto a memory device or connecting to an external computing device. Any appropriate programming mode can be employed. In some examples, pre-determined sequences of presses of the dose request button 304 could be used to enter programming commands. In some examples, the short-range non-contact identifier 306 could read codes of one or more special tags to enter, authorize, or authenticate programming commands. In some examples, a dose request device 300 could employ a learning mode in which the short-range non-contact identifier 306 could be used to read an identification code from a tag, which could be deemed an authorized identification code by merit of having been read while in the learning mode. It is to be appreciated and understood that the aforedescribed systems, devices, and methods are just some examples pertaining to the novel and inventive subject matter hereof.

In some example medicament delivery systems such as system 100, a dose request device such as devices 150 or 300 may not always necessarily perform a determination of whether an identification code read by the dose request device matches an authorized identification code. The dose request device could, for example, communicate an identification code that it reads to a medicament delivery device (such as device 102 or 202), where the determination could be performed. The medicament delivery device, after performing the determination, could then appropriate respond to a dose request conveyed from the dose request device, depending on the positive or negative result of the determination. In some examples, the medicament delivery device, after performing the determination, can communicate the positive or negative result of the determination back to the dose request device that provided the read identification code, which in turn could provide an indication to a user based at least in part upon the result of the determination. In some examples, after receiving such information from the medicament delivery device, the dose request device, upon subsequent reads of the same identification code, could perform the determination as to whether the same read identification code was authorized or not, without relying upon the medicament delivery device to perform the determination. Other scenarios for information handing and determination of identification code authorization are contemplated. For example, the determination of whether an identification code read by a dose request device is authorized could be performed at an EMR or HIS system such as system 105, after receiving a read identification code communicated from the dose request device either directly or routed through a medicament delivery device, or by any other suitable path. The EMR or HIS system could then communicate the results of its determination to the dose request device and/or medicament delivery device for appropriate further action consistent with the determination. After receiving information from the EMR/HIS system, either the dose request device and/or medicament delivery device could perform subsequent identification code authorization determinations consistent with the determination performed by the EMR/HIS system, without necessitating further involvement of the EMR/HIS system.

In some examples, dose request devices can be used for additional access control functionality beyond dose request authentication. For example, reading of identification codes from tags could be used to help control access to pump settings such as flow rate, clinician boluses, infusion parameters, and any other appropriate settings. A dose request device could simply pass identification codes to a medicament delivery device, EMR, or HIS system, any of which could be configured to determine whether an identification code is associated with a user authorized to access settings, or a dose request device could check itself for a match between an identification code read from a tag and a list of users authorized to access pump settings, and pass along an appropriate indication of its findings to the pump.

Dose request device 300 can be powered by any suitable means. When the communication interface communicatively couples to a medicament delivery device by way of a hard wired connection, as for example via a known dose request device jack that is configured to provide electrical power via conductors, the dose request device can draw power via the hard wired connection. The dose request device 300 can include any suitable energy storage component(s), such as a chemical battery or capacitor. The energy storage component(s), if present, can be disposable or rechargeable. Rechargeable energy storage component(s) can be recharged by any suitable means, such as via a hard wired communication link, or by another wired connection, which may be transient. Other energy sources, such as energy harvesting devices, may also be contemplated. In some examples, a dose request device can lack an energy storage component with sufficient capacity to power the device for more than a brief interruption of a hard wired power supply.

Figure 4:
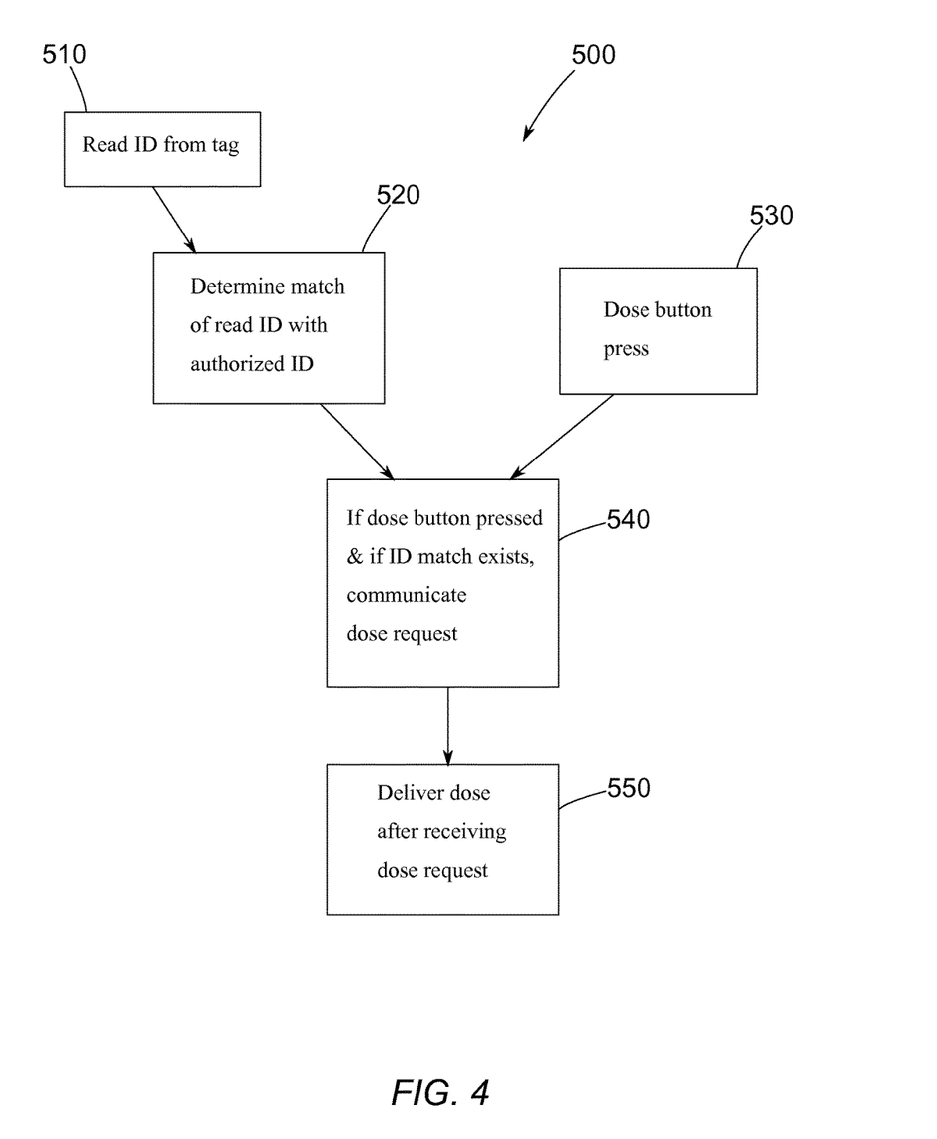
FIG. 4 is a schematic flow diagram of a method of providing a medicament from a medicament delivery device.

The present disclosure contemplates a method 500 of providing a substance from a medicament delivery device, illustrated in the flow diagram of FIG. 4. Method 500 can be performed with a medicament delivery system like or similar to delivery system 100 of FIG. 1, in any of the many possible compatible variations contemplated in the present disclosure. The medicament delivery device can be communicatively coupled to a dose request device like or similar to dose request device 300 in any of the many possible compatible variations contemplated in the present disclosure. Method 500 can include, at 510, a short-range non-contact identifier of the dose request device reading or attempting to read an identification code from a tag. Method 500 can include, at 520, a controller of the dose request device determining whether the identification code read by the short-range non-contact identifier matches an authorized identification code of a set of one or more authorized identification codes. At 530, an individual can press the dose request button of the dose request device. Method 500 can include, at 540, the controller, if the dose request button is pressed and if the identification code read by the short-range non-contact identifier matches the authorized identification code, communicating a dose request to the medicament delivery device via a communication interface of the dose request device. Method 500 can include, at 550, the medicament delivery device delivering a dose after receiving the dose request from the communication interface of the remote dose apparatus. Any or all of 510-550 of method 500 can be repeated such that the medicament delivery device can deliver another dose after receiving another dose request from the communication interface of the dose request device.

While the description of method 500 may imply a particular temporal sequence, any such implied sequence should not be considered limiting. For example, reading or attempting to read an identification code from a tag at 510 can precede or follow a press of a dose request button, as discussed elsewhere herein. Also, not all steps necessarily need be repeated every time to result in subsequent dose requests and/or deliveries after a first dose request/delivery. For example, in some cases a match of an identification code read by the short-range non-contact identifier with an authorized identification code can be considered to be valid for a defined period of time, during which a subsequent press of the dose request button can result in communication of another dose request, without necessarily requiring repeating 510 and 520.

The disclosure should not be considered limited to the particular examples described herein, but rather should be understood to cover all aspects of the disclosure and equivalents thereof. Various modifications, equivalent processes, as well as numerous structures to which the disclosure can be applicable will be readily apparent to those of skill in the art upon review of the instant specification.

What is claimed is:

1. A dose request device for a medicament delivery device, comprising:
    a housing;
    a dose request button associated with the housing;
    a short-range non-contact identifier associated with the housing, the short-range non-contact identifier being capable of reading an identification code from a tag when the tag is disposed within a first range and not being able to read the identification code from the tag when the tag is disposed beyond a second range;
    a communication interface configured to communicate with the medicament delivery device;
    a controller operatively coupled to the dose request button, the short-range non-contact identifier, and the communication interface, the controller configured and programmed to:
        determine whether the identification code read by the short-range non-contact identifier matches any authorized identification code of a set of one or more authorized identification codes; and
        if the identification code read by the short-range non-contact identifier matches any authorized identification code of the set of one or more authorized identification codes, and if the dose request button is pressed, communicate a dose request to the medicament delivery device via the communication interface, and
        if the identification code read by the short-range non-contact identifier does not match any authorized identification code of the set of authorized identification codes, and if the dose request button is pressed, not communicate the dose request to the medicament delivery device via the communication interface.

2. The device of claim 1, wherein when the controller communicates the dose request to the medicament delivery device, the controller also communicates that the dose request is an authorized dose request.

3. The device of claim 1, wherein when the controller communicates the dose request to the medicament delivery device, the controller also communicates the identification code read by the short-range non-contact identifier to the medicament delivery device.

4. A dose request device for a medicament delivery device, comprising:
    a housing;
    a dose request button associated with the housing;
    a short-range non-contact identifier associated with the housing, the short-range non-contact identifier being capable of reading an identification code from a tag when the tag is disposed within a first range and not being able to read the identification code from the tag when the tag is disposed beyond a second range;
    a communication interface configured to communicate with the medicament delivery device;
    a controller operatively coupled to the dose request button, the short-range non-contact identifier, and the communication interface, the controller configured and programmed to:
        determine whether the identification code read by the short-range non-contact identifier matches any authorized identification code of a set of one or more authorized identification codes; and
        if the identification code read by the short-range non-contact identifier matches any authorized identification code of the set of one or more authorized identification codes, and if the dose request button is pressed, communicate a dose request to the medicament delivery device via the communication interface, and
        if the identification code read by the short-range non-contact identifier does not match any authorized identification code of the set of authorized identification codes, and if the dose request button is pressed, communicate a non-authorized dose request to the medicament delivery device via the communication interface.

5. A dose request device for a medicament delivery device, comprising:
   a housing;
   a dose request button associated with the housing;
   a short-range non-contact identifier associated with the housing, the short-range non-contact identifier being capable of reading an identification code from a tag when the tag is disposed within a first range and not being able to read the identification code from the tag when the tag is disposed beyond a second range;
   a communication interface configured to communicate with the medicament delivery device;
   a controller operatively coupled to the dose request button, the short-range non-contact identifier, and the communication interface, the controller configured and programmed to:
      determine whether the identification code read by the short-range non-contact identifier matches any authorized identification code of a set of one or more authorized identification codes; and
      if the identification code read by the short-range non-contact identifier matches any authorized identification code of the set of one or more authorized identification codes, and if the dose request button is pressed, communicate a dose request to the medicament delivery device via the communication interface, and
      if the identification code read by the short-range non-contact identifier does not match any authorized identification code of the set of authorized identification codes, and if the dose request button is pressed, communicate a non-authorized dose request to the medicament delivery device along with the identification code read by the short-range non-contact identifier.

6. The device of claim 1, wherein the controller is configured and programmed to:
   if the short-range non-contact identifier fails to read an identification code, and if the dose request button is pressed, not communicate the dose request to the medicament delivery device via the communication interface.

7. The device of claim 1, wherein the controller is configured and programmed to:
   if the short-range non-contact identifier fails to read an identification code, and if the dose request button is pressed, communicate a non-authorized dose request to the medicament delivery device via the communication interface.

8. The device of claim 1, wherein the controller is configured and programmed to:
   if the short-range non-contact identifier fails to read an identification code, and if the dose request button is pressed, communicate a non-identified dose request to the medicament delivery device via the communication interface.

9. The device of claim 1, wherein the communication interface is configured to communicate with the medicament delivery device via a wired connection.

10. The device of claim 1, wherein the communication interface is configured to communicate with the medicament delivery device via a wireless connection.

11. The device of claim 1, wherein the short-range non-contact identifier is an RFID device, and the tag is an RFID tag.

12. The device of claim 1, wherein the controller is configured and programmed to command the short-range non-contact identifier to attempt to read the identification code from the tag when the dose request button is pressed.

13. The device of claim 1, wherein the controller is configured and programmed to command the short-range non-contact identifier to attempt to read the identification code from the tag when the dose request button is pressed only if a time interval since a most recent preceding match of an authorized identification code exceeds a predetermined time interval.

14. The device of claim 1, wherein the short-range non-contact identifier is configured to periodically attempt to read the identification code from the tag, either under command from the controller, or independently of the controller.

15. A dose request device for a medicament delivery device, comprising:
   a housing;
   a dose request button associated with the housing;
   a short-range non-contact identifier associated with the housing, the short-range non-contact identifier being capable of reading an identification code from a tag when the tag is disposed within a first range and not being able to read the identification code from the tag when the tag is disposed beyond a second range;
   a communication interface configured to communicate with the medicament delivery device;
   a controller operatively coupled to the dose request button, the short-range non-contact identifier, and the communication interface; and
   a memory operatively coupled to the controller, the controller configured and programmed to:
      determine whether the identification code read by the short-range non-contact identifier matches any authorized identification code of a set of one or more authorized identification codes; and
      if the identification code read by the short-range non-contact identifier matches any authorized identification code of the set of one or more authorized identification codes, and if the dose request button is pressed, communicate a dose request to the medicament delivery device via the communication interface,
   the controller configured and programmed to store in the memory a log of presses of the dose request button along with, for each of the presses, a corresponding identification code or a lack of identification code.

16. The device of claim 1, further comprising an indicator disposed with the housing that communicates an identification and/or dose request status.

17. The device of claim 1, wherein the dose request does not identify a type of medicament requested.

18. The device of claim 1, wherein the second range is about 15 cm.

19. A medicament delivery system comprising:
   a medicament delivery device, including:
      a container configured to house a plurality of doses of a medicament;
      a controller configured to command release of a dose of the medicament upon receipt of a dose request if dose release criteria are satisfied; and
      a communication interface operatively coupled to the controller, the communication interface configured to receive a dose request from external the medicament delivery device and relate the dose request to the controller; and a dose request device, including:
  a housing;
  a dose request button disposed with the housing;
  a short-range non-contact identifier associated with the housing, the short-range non-contact identifier being capable of reading an identification code from a tag when the tag is disposed within a first range and not being able to read the identification code from the tag when the tag is disposed beyond a second range
  a communication interface configured to communicate with the medicament delivery device;
  a controller operatively coupled to the dose request button and the short-range non-contact identifier, the controller configured and programmed to:
    determine whether the identification code read by the short-range non-contact identifier matches any authorized identification code of a set of one or more authorized identification codes; and
    if the identification code read by the short-range non-contact identifier matches any authorized identification code of the set of one or more authorized identification codes, and if the dose request button is pressed, communicate a dose request to the medicament delivery device via the communication interface,
wherein the medicament delivery device is configured to house and release only a single variety of medicament.

20. A medicament delivery system comprising:
a medicament delivery device, including:
  a container configured to house a plurality of doses of a medicament;
  a controller configured to command release of a dose of the medicament upon receipt of a dose request if dose release criteria are satisfied; and
  a communication interface operatively coupled to the controller, the communication interface configured to receive a dose request from external the medicament delivery device and relate the dose request to the controller; and
a dose request device, including:
  a housing;
  a dose request button disposed with the housing;
  a short-range non-contact identifier associated with the housing, the short-range non-contact identifier being capable of reading an identification code from a tag when the tag is disposed within a first range and not being able to read the identification code from the tag when the tag is disposed beyond a second range
  a communication interface configured to communicate with the medicament delivery device;
  a controller operatively coupled to the dose request button and the short-range non-contact identifier, the controller configured and programmed to:
    determine whether the identification code read by the short-range non-contact identifier matches any authorized identification code of a set of one or more authorized identification codes; and
    if the identification code read by the short-range non-contact identifier matches any authorized identification code of the set of one or more authorized identification codes, and if the dose request button is pressed, communicate a dose request to the medicament delivery device via the communication interface,
wherein the medicament delivery device includes an infusion pump.

21. A medicament delivery system comprising:
a medicament delivery device, including:
  a container configured to house a plurality of doses of a medicament;
  a controller configured to command release of a dose of the medicament upon receipt of a dose request if dose release criteria are satisfied; and
  a communication interface operatively coupled to the controller, the communication interface configured to receive a dose request from external the medicament delivery device and relate the dose request to the controller; and
a dose request device, including:
  a housing;
  a dose request button disposed with the housing;
  a short-range non-contact identifier associated with the housing, the short-range non-contact identifier being capable of reading an identification code from a tag when the tag is disposed within a first range and not being able to read the identification code from the tag when the tag is disposed beyond a second range
  a communication interface configured to communicate with the medicament delivery device;
  a controller operatively coupled to the dose request button and the short-range non-contact identifier, the controller configured and programmed to:
    determine whether the identification code read by the short-range non-contact identifier matches any authorized identification code of a set of one or more authorized identification codes; and
    if the identification code read by the short-range non-contact identifier matches any authorized identification code of the set of one or more authorized identification codes, and if the dose request button is pressed, communicate a dose request to the medicament delivery device via the communication interface,
wherein the dose of the medicament is provided in an orally-ingestible solid.

* * * * *